United States Patent [19]

Kiyasu

[11] 4,248,642
[45] Feb. 3, 1981

[54] WASH CYCLE PROCESS

[76] Inventor: John Y. Kiyasu, 94 Meadow St., Garden City, N.Y. 11530

[21] Appl. No.: 18,817

[22] Filed: Mar. 8, 1979

[51] Int. Cl.$^3$ .............................................. B08B 3/08
[52] U.S. Cl. ........................................ 134/2; 134/3; 134/10; 134/22 C; 134/26; 134/28; 134/29
[58] Field of Search ...................... 134/10, 2, 3, 22 C, 134/26, 28, 29; 422/28, 31, 36, 37

[56] References Cited

U.S. PATENT DOCUMENTS

| | | | |
|---|---|---|---|
| 2,134,679 | 11/1938 | Allen | 422/28 X |
| 3,139,323 | 6/1964 | Shields et al. | 422/37 X |
| 3,282,775 | 11/1966 | Stonehill | 422/36 X |
| 3,739,791 | 6/1973 | Fry et al. | 422/28 X |
| 3,819,329 | 6/1974 | Kaestner et al. | 422/37 X |
| 4,169,123 | 9/1979 | Moore et al. | 422/28 X |

*Primary Examiner*—Marc L. Caroff
*Attorney, Agent, or Firm*—E. Janet Berry

[57] ABSTRACT

A systematic and programmed wash cycle for cleaning automatic and semi-automatic biochemical analyzers and separators and other equipment. The wash cycle includes a series or sequence of specific and ordered washing steps using a fixed specific sequence of reagents in critical concentrations including use of a hypochlorite reducing agent, a peroxide oxidising agent, an alkaline hydroxide solution, a solution of cetyl pyridinium bromide and cinnamic aldehyde, a solution of a polysulfonated alkyl detergent and a hydrochloric acid solution. It is also contemplated as a special feature, to use a so-called "polishing" system to eliminate from analyzers the micro-organisms and enzymes which cause interference with UV analyses. It is also a particular feature that the ordered wash cycle can be used to clean tubular flow systems, including piping and plumbing, such as may occur in centralized air conditioning units and miscellaneous washing machinery.

9 Claims, 7 Drawing Figures

FIG. 1.
THE HYPOTHETICAL ANATOMY OF MICROBIAL INVASION
(LAYERED NATURE OF MICROORGANISM GROWTH AND FLORA)
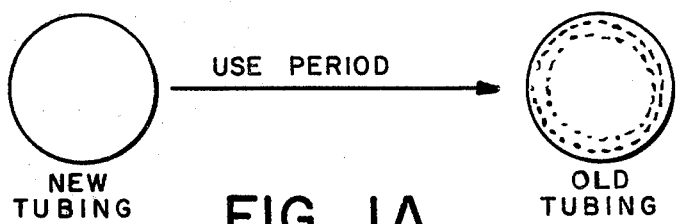
FIG. 1A.
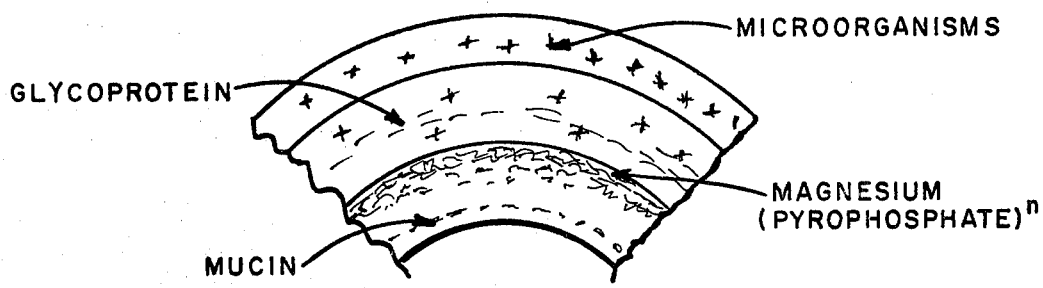
FIG. 2.
WASH CYCLE CARTRIDGE
FIG. 2A.
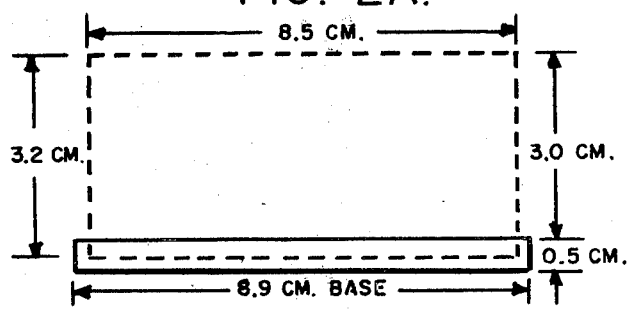
FIG. 2C.
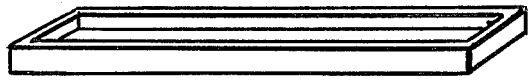
BASE RETAINER
OUTER DIMENSION: 0.5 X 1.6 X 8.9 CM.
INNER  "  0.3 X 1.2 X 8.5 "
FIG. 2B.
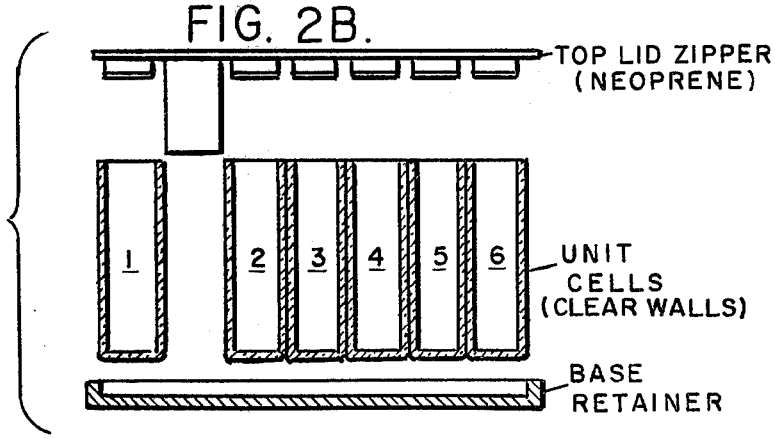
FIG. 2D.
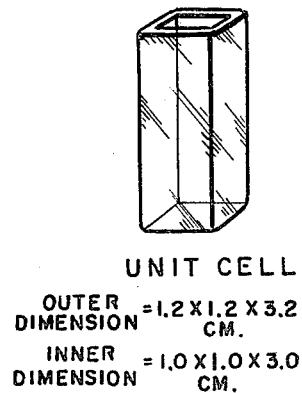
UNIT CELL
OUTER DIMENSION = 1.2 X 1.2 X 3.2 CM.
INNER DIMENSION = 1.0 X 1.0 X 3.0 CM.

WASH CYCLE PROCESS

This invention generally concerns a novel systematic procedure or method for the thorough and efficient cleaning of automated and semi-automated enzyme analyzers and other such equipment as well as larger equipment. The invention can be appropriately described as a "shot-gun" wash cycle technique. There is used a specific protocol or specific sequence or series of especially selected cleansing fluids. The specific sequence and the implementation of their use can be conveniently marketed and employed in a particular package or kit form, as a further feature of the invention.

Although biochemists and various other laboratory workers are thoroughly aware of detrimental microbial effects on enzyme analyses, co-factors, inhibitors, receptors, and the like, a general laxness causes many of them to ignore such considerations and not to take suitable precautions therefor. At the present time, automated and semi-automated enzyme analyzers continue to use more sensitive techniques especially such as they may involve multiple coupled reactions and immuno-enzyme reactions. The effect of coatings, sludges, and layers of microbial flora, residues, and such contaminants can become significant in these new procedures. However, these effects are usually so gradual that, on a day-to-day or week-to-week basis, the operator may well not notice the changes produced even though serious errors may be the result.

Also it is a critical feature that an ordered cycle of wash reagents are necessary for the cleansing of tubular flow systems when objects such as laboratory glassware, beakers, tubing and the like are to be effectively cleaned in glassware washers similar to commercial or automatic dishwashers. For example, it is obvious that analytical instruments cannot be cleaned with steaming hot wash reagents because of friability of the instrumentation and also the plumbing components. Furthermore, in analytical instruments, the use of abrasives such as aluminates or silicates cannot be tolerated because of scratching or etching effects.

The mechanism involved in the washing cycle of the invention may involve chemical scrubbing effects wherein contaminating tubular residues are denatured, dissolved, flocculated, gas-permeated, coagulated, co-precipitated, or undergo several of these descriptive processes involving chemical interactions, which are essentially independent of mechanical forces. For example, and by comparison, any of the wash cycle reagents alone are effective in clearing containers or beakers provided mechanical scrubbing can conveniently be instituted along with that reagent, such as scrubbing with glass beads, sand, cotton gauze and the like. As a further example, tubular systems suffer from lack of mechanical physical accessability and the use of abrasives are not suitable. For example, if an entire central air-conditioning piping system is to be cleaned, the use of semi-suspendable abrasives such as sand and other scouring material would not be suitable or practical even at the macro-level, since the pumps involved in such a system would become clogged or inoperable.

Common abbreviations will be used throughout the remainder of this discussion. The known meanings of these abbreviations are as follows:
CPK-MB = creatine phosphokinase, isoenzyme II (composed of M and B monomers as a hybrid dimer) and found only in the myocardium;
BUN = blood urea nitrogen;
DPN (NAD) = diphospho pyridine nucleotide otherwise known as nicotinic acid adenine dinucleotide;
DPNH (NADH) = the reduced form of the above;
TPN (NADP) = triphospho pyridine nucleotide otherwise known as nicotinic acid adenine dinucleotide, phosphorylated;
O.D = optical density;
E = enzyme.

In the simplest version of the invention, a cleaning cycle is used to clean the internal plumbing of flow-through instrumentation or dilutors, such as, for example, a miniscule sewer pipe or plumbing which is exposed from time to time to a variety of chemicals and organisms. At a macro level of inspection it is easy to detect layer upon layer (multilayers) of solidified encrustations sandwiched between and interspersed with mosaics of microorganisms, encrustations, slime and microbiological sludge. The use of cleaning aids such as abrasives, wire brushes, caustic lye, chromic acid-sulfuric acid mixtures, and the like ar all mechanisms for cleaning these accumulated films and debris where the surfaces are accessible. These techniques, however, are not available for cleaning operations in analytical instrumentation because of the miniscule diameter of tubing as well as inaccessability and friability of equipment. In addition to these difficulties, it is not at all predictable what kind of microbial flora or films can be generated in daily usage of instrumentation. Furthermore since obviously an "infected" analytical system cannot by systematically produced, it is difficult to plan and execute a series of meaningful experiments to duplicate and to define exactly how a cleaning or wash cycle should be programmed.

Although laboratory observations have been made as to microbial contamination of water baths, incubating devices and other such devices, the routine use of degrading hypochlorite solutions has not been effective in instrumentation and equipment perhaps because of microbial mutations, adaptations, or lack of sufficient scrubbing action.

These deleterious effects are most pronounced at low enzyme levels, in environments where the germs, receptors, or contaminants compete successfully for the substrate formulation. The laboratory control sera, and such materials are usually at a higher level of enzyme concentration. The best case in point is CPK-MB - a measurement which quite often must be at 10 mIU/ml or less. The wash cycle invention process was, in fact, discovered in response to a need to provide reliable CPK-MB values as they are related to and an indication of, myocardial infarcts.

It is the essence of the invention to carry out the successful wash cycle using a cycle or series of specified reagents in prescribed order. The reason for using this fixed cycle is that just as in a washing machine cycle, each phase of the cycle has a special function. In the case of the wash cycle of the invention, each reagent also has a function and in addition, the order of the wash reagents is most important. Each reagent and its order in sequence is critical otherwise the equipment will not be satisfactorily cleansed.

The minimum sequence of reagents which is used in carrying out the process of the invention may be outlined as follows: 1% to 5% sodium hypochlorite, 1% to 6% hydrogen peroxide, 0.05 to 0.2 N NaOH, cetyl pyridinium bromide/cinnamaldehyde, polysulfonated detergent and 0.05 to 0.2 N HCl.

The essential wash cycle consists of:
(a) 2% to 10% Sodium Hypochlorite (5% preferred)
(b) 2% to 10% Hydrogen Peroxide (5% preferred)
(c) 0.1 to 0.5 N Sodium Hydroxide (0.2 N preferred)
(d) 1% to 5% Cetyl Pyridinium Bromide (2% preferred), 0.05 to 0.2% Cinnamic Aldehyde (0.1% preferred)
(e) 10% to 50% Detergent (polysulfonated detergent or equivalent) (20% preferred)
(f) 0.1 to 0.5 N Hydrochloric Acid (0.2 N preferred)

Each of these six washing cycle steps is preferably interrupted with intervening water wash steps. The quality of the water should be equivalent to that of triple distilled, reagent grade water which is free of microbial or other contaminants. This wash cycle should be instituted in the laboratory at least once each week, preferably at the end of the working week. This procedure can for instance be instituted on any automated, semi-automated enzyme analyzer especially where syringe, pumps or tubing are involved. It can also be used on auto-dilutors and other such equipment. The full wash cycle should take approximately one hour.

It is also possible to modify the sodium or potassium hydroxide or hydrochloric acid wash by the addition of trypsin to the former and pepsin to the latter as these are proteolytic agents with appropriate and respective optimum pH values. The extension of this feature to the use of other degrading enzymes such as lysozyme, glycosidases, dextranase, should be cautions and may be counter-productive, since new symbiotic strains of microbial contamination may well eventually ensue.

The combination of cetyl pyridinium bromide with cinnamic aldehyde is probably advantageous for co-precipitating micro-organisms and other residues and sludges as they appear to co-precipitate together. This is probably a significant feature of the invention since other materials containing cetyl pyridimium bromide but no cinnamic aldehyde do not appear to be as efficacious for the successful operation of the wash cycle of the invention. As an indication of one function of the cinnamic aldehyde, it appears that this material functions as a kind of "chromogenic" indicator. Thus, if 0.1 N sodium hydroxide is mixed with cetyl pyridinium bromide in the presence of cinnamic aldehyde a copious amount of white precipitate is formed. If the system has also microorganisms present, the precipitate formed is colored varying in shades of brown, orange or red. If the cinnamic aldehyde is not present, this effect is not seen.

For comparison purposes, all of the wash cycle reagents alone have been tested as cleansing agents on the Beekman TR with unsatisfactory results. The alkali wash followed by the acid wash, used routinely in most clinical laboratories or for many analytical instruments such as the Technicon SMA 12/60 or SMA 6/60 or the Gilford 300-N, have also been found unsatisfactory for consistent reliable analyses employing "UV" chemistries such as CK-MB. The use of a sequence of alkali-hypochlorite-acid washes has also been found to be unsatisfactory. No three components of the wash cycle used in any order has appeared to be effective in cleaning a contaminated analytical system. These negative results cannot be exactly duplicated since one cannot experimentally infect a system. Weeks of daily abuse and use are required for a mosaic of microorganisms and residue to present itself as an analytical problem. We assume that since we have finally resolved the total infectivity problem with the complete wash cycle, the contamination is heterogeneous and not necessarily the same in each instance (i.e., collected encrustations, residues, slime and microbiological sludges). For instance, FIG. 1 shows a clean tube, a layered microbial contamination and an enlarged view of the layer of sludge and residues requiring cleaning. However, the wash cycle as described meets almost all of the anticipated contamination problem since it has experimentally solved all of the infectivity problems in a typical hospital laboratory. The UV polisher, however, is an important modification to cover new analytical systems and microbial/enzyme exposure.

In order to facilitate this wash cycle as a laboratory routine, especially in clinical laboratories, this series of reagents can be packaged in disposable plastic cartridges. Although reagent a) and reagent b) are quite dilute, they should not be permitted to mix in transit, in storage or in use. Therefore, the six (6) pack cartridges may have, for example, an empty air cell which physically separates reagent a) from reagent b). Further, this empty cell should be vented. All other chambers should be equipped with leak-proof, plastic seals, preferably in a ribbon configuration, so that the chambers can be opened in their proper sequence. FIG. 2 shows a typical embodiment of this feature of the invention.

To refer to FIG. 2, the wash cycle cartridge has six compartments numbered respectively from 1 to 6, with an empty chamber labeled 0 (zero). The reagents supplied will generally serve the following functions:

| | |
|---|---|
| (a) | 1 = reducer |
| | 0 = air/water |
| (b) | 2 = oxidizer |
| (c) | 3 = base (alkali) |
| (d) | 4 = astringent |
| (e) | 5 = detergent |
| (f) | 6 = acid |

The use of the ordered series of reagents in the so-called wash cycle has been shown to have the following effects: kills(hypochlorite→$H_2O_2$), dissolves (NAOH), precipitates (cetyl pyridinium bromide), suspends (detergent), cleanses (HCl) in an order such that no microorganism can adapt nor do appendages or filamentous material remain to adhere to solid/liquid interfaces.

In states or areas where 5% or higher hydrogen peroxide is not permitted to be handled by conventional delivery systems reagent 2) can be eliminated, and instruction inserts supplied which advise filling such an empty compartment just prior to use with 5% or higher concentration of hydrogen peroxide.

At least two sizes are contemplated as available in the kits: a small cartridge (3 cm×1 cm×7 cm) for sipper systems and an intermediate size for auto-analyzers and instruments (5 cm×2 cm×9 cm). These packages are meant to be used one time only, thence discarded.

The pre-packaged kit module is extremely desirable from a practical application aspect because its use insures that the laboratory technologist is "forced" to go through the entire wash cycle process in the appropriate sequence of steps. Such a package concept has not previously been put into commercial application. This is probably because it has been believed that a contamination problem is due to a singular causative agent whereas the problem is in fact a heterogeneous causative problem which is not solved by isolated steps or conventional cleaning methods.

The wash cycle herein described and which is the main feature of the invention is especially adapted for in situ washes of tubular flow analytical instrumentation such as continuous flow, sipper cuvettes, blood/gas instruments, pH meters, autodilutors and the like. This list of equipment which may be cleaned by the invention method is in no way intended to be all inclusive but is submitted as examplary only.

The wash cycle appears to scrub out microbial contaminants and residues, and in that manner minimizes analytical background "noise".

This wash cycle can be instituted also for bulkier containers and devices such as the power cell used in electrophoresis, volumetric flasks, auto-dilutors and auto-pipettes. Here Q-tips or cotton swabs may be used for carrying out the scrubbing action. Containers such as volumetric flasks are more readily scrubbed with the appropriate sequenced reagents and also by the addition of a thimble full of reagent grade Sea-Sand or inert glass beads.

It is entirely possible to use the process on a macroscale for external uses such as in programmed washing devices where for cost reasons or otherwise the reagents will be re-used over again with suitable water rinses such that the reagents will not be contaminated with each other. Although this process is not intended to function for sterilization, in effect the results may be sufficiently thorough to allow laboratory disposables to be so treated prior to discarding. For example, a number of regulatory agencies are presently proposing the steam autoclaving of all "potentially" infectious agents and devices prior to garbage disposal. The process of the invention may well be considered a practical and economical alternative to that step.

It is believed that the wash cycle components and sequence is very important to proper laboratory operations. As one alternative to the wash cycle described herein, it may be possible to wash exhaustively the instrumentation daily with one or more washing agents such as acid, base or both and/or with a detergent. However, in most cases such routine washing cannot be maintained where the instrument is in continuous use. In such cases the wash cycle of the invention is advantageously employed to clean the system. This is especially true where it is necessary to monitor instrumentally extremely low signals of enzyme activity.

Although the "shot gun" wash cycle was designed primarily for the orderly cleansing of the internal plumbing of analytical instrumentation, dilutors, or any other flow-through devices, which may become contaminated with micro-organisms, solidified enzymes and other interfering contaminants, some industrial applications for the invention are contemplated. It is useful as an orderly method of "sterilizing" disposables prior to garbage discard, i.e., prerequisites of disposing "non-infectious" garbage. Such a cleaning method may recycle each reagent (i.e. 1→7) as a cost saving device. The routine cleansing of hospital or restaurant garbage cans or refuse containers is one such application. The same considerations of "sterilizing" analytical instrumentations (i.e., avoiding toxic, caustic, "harmful" reagents) apply also for other industrial uses.

A second "industrial" application of the "wash cycle" method of the invention may be applied on a macro-scale for all the plumbing, tubing, and cooling towers of central air conditioning units - which have recently been implicated in the sporadic outbreak of the so-called "Legionnaires Disease". The Philadelphia outbreak was almost certainly caused by atomization of the micro-organism of air-cooling condensates harboring the pathogen(s). Obviously such central air-conditioning and heating systems, including red-wood lined cooling towers and the like, cannot be "autoclaved" by steam sterilization, or other laborious techniques without closing down the affected institution or perhaps, damaging or destroying equipment. On this macro-scale, the same configuration of the wash cycle reagents (1→7) can be incorporated into the plumbing system, as if the entire air conditioning duct and plumbing system were envisioned as a huge scale model of the internal plumbing of an analytical instrument. Thus the invention cleaning process can also be used for these purposes.

It is entirely practical to use the wash cycle cleaning principle for the plumbing systems of large institutional air conditioning systems. It is also a practical approach having great advantages to "sterilize" plumbing systems prone to microbial infestation.

Thus in such huge scale applications the volume of each wash cycle reagent (1→7) would be for instance 400 gallons or multiples thereof, and it may be more feasible to recover each reagent as an economical measure, and also so this wash cycle may be instituted once per month or intermediates thereof, similar to the ordered maintenance of laboratory instrumentation.

Thus, the application of the wash cycle invention to garbage disposables, air conditioning equipment, water baths, and the like is also entirely feasible. A larger expansion of these applications can be applied to the cleaning of swimming pools, fish hatcheries, water storage tanks, and, most importantly, large centralized air conditioning systems, containing many feet of recirculating plumbing (piping). The use of the wash cycle concept on cooling towers and associated plumbing is also applicable. It may be noted that the Philadelphia outbreak of Legionnaires Disease was caused by microbial flora in the ventilation system. Again, the classical concept of cleaning any of the above mentioned systems conventionally is a single-pronged attach such as chlorine, detergent, or fumigant. Multi-programmed wash cycles of the type described herein using a predetermined series of sequential steps have not previously been disclosed or used.

As an additional feature, it is also possible to introduce a "polisher" into the wash cycle procedure. Clinical laboratories are increasingly using enzymes as reagents for example, to measure the concentration of solutes in biological fluids such as glucose (hexokinase, glucose oxidase, etc.), BUN (urease), uric acid (uricase), cholesterol (cholesterol oxidase, cholesterol esterase), thyroxine (malate dehydrogenase), as well as other natural and pathological materials of varying concentrations. It is apparent that many of these enzyme reagent formulations are made of crude microbial preparations and may contain other contaminating enzymes, which, however, do not react with the particular analyte. Since the same instrument is used, however, for the analyses of different analytes with different enzyme or microbial extracts, the distinct possibility arises for cross interaction, especially if the flow through cuvette or plumbing of the spectrophotometer or other analytical instrument contains vestiges of organisms or enzymes, which may well interfere with other "chemistries".

A number of different "polishers" to the wash cycle can be employed. One "polisher" which is effective is primarily for the use of UV chemistries (analyses employing ΔO.D. changes at 340 mμ) where DPN is converted to DPNH (NAD→NADH). One important application is to reduce the background noise apparent for CK-MB determinations using the Rosalki substrate which follows the rate of change (ΔO.D.$^{340}$). This application is for a DPN or TPN-linked dehydrogenase step and will henceforth be termed the "UV polisher".

It has been found that after an extended use, approximately one year, of a flow-through sipper cuvette (Beckman 24/25) generally considered "noise" free, a number of CK-MB fractions known to be free of CK activity (Beckman TR) were observed to give erratic CK signals, although the Rosalki substrate itself, was "noise-free". This obviously means that some solute in the MB fraction which served as a substrate for an enzyme, entirely different from the Rosalki formulation, but which however utilized the co-factor DPN and was converting it to DPNH. It was established to be cuvette contamination with an alcohol dehydrogenase. Remarkable O.D.$^{340}$ changes were seen by feeding the sipper 10 percent methanol. Although the dead-end product should be E-formaldehyde, the suppression of "noise" was only temporary. Feeding the sipper 40 percent formalin (formaldehyde) did not kill this noise. Many enzyme substrate formulations contain stabilized enzymes treated with ethylene glycol, glycerol, maltose, and the like for formulation stability. Not surprisingly these contaminants accurue in flow-through systems which receive a variety of microbial and enzyme formulations and are quite hardy and persistent.

It has been discovered that after the use of the novel wash cycle herein described which results in layers of different organisms and enzymes stripped down and collected, any contaminants present are prone to and available for a full-kill attack.

This can be achieved by going back to Wash Solution #1 indicated as Chlorox (hypochlorite) and allowing a soaking for a minimum of five minutes for a "kill" period.

This "kill" is then finished by the sipping of 50% methanol. As the spectrophotometer setting is set at 340 mμ-the 50% methanol is allowed to "soak" in the 37° C. cuvette until the 340 O.D. no longer changes. This "soaking" should be for a period of 10 to 20–30 minutes. When the O.D. no longer changes, fresh 50% methanol is aspirated into the cuvette, the O.D. should be no different than a water blank (i.e. 0.000). The O.D.$^{340}$ should now not change with either 10% methanol or 50% methanol. The use of 50% methanol, after the wash cycle, and hypochlorite constitutes the steps of carrying out the "UV" polisher system.

To summarize, a polisher for UV chemistries has been discovered with the objective to eliminate organisms and enzymes which normally interfere with UV analyses, thus making analytical systems noise-free. As a result, extremely low levels of enzyme (UV) activities can be measured for instance, CK-MB using the Rosalki substrate. Since 40% formaldehyde does not kill residual UV activity, the efficacy of 50% methanol following a wash cycle, and the hypochlorite soak are envisioned as:

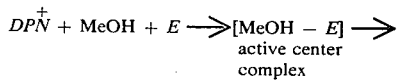

-continued

[Formaldehyde − $E$] + $DPNH$ + H$^+$
dead-end
Inhibitor complex

If an innocuous suspensoid which is also a mild abrasive can be incorporated into the wash cycle, then the wash cycle would be even more effective. Thus it is contemplated as useful and as an additional feature of the present wash cycle to incorporate an "abrasive" step.

EXAMPLE 1

The sequence of wash solution steps was established in attempts to clean out an infected Bechman TR Enzyme Analyzer. Repeated cultures of different sediments and slime by standard microbial culture identification techniques were highly unsatisfactory such as "many pseudomonas", or gram negative rods. Thus, it was found that the resulting order of wash reagents was desirable and of great advantage since this ordered wash cycle solved the problem of repeated "infectivity".

When sodium hypochlorite and hydrogen peroxide are admixed there occurs effervescence with the generation of chlorine gas and oxygen. The peroxide is reduced to water and, in effect, the chlorite is oxidized by the peroxide. Both of these reagents alone are antiseptic (kills organisms), but each of these along has been found to be inadequate. The sipper cuvette and tubing of "non-wettable" hard polyethylene has been observed to effervesce on miniscule loci on the inner wall of such tubing in contaminated systems, indicating that miniscule loci of deposits of debris and organic matter may be embedded at these sites. The hypochlorite is believed to permeate this miniscule matrix and, when the peroxide then bathes this environment, the microsites of effervescence of the above mentioned interaction loosens these micro-deposits.

When the alkali wash is then instituted, the loosened micro-deposits are further solvated by the excess hydroxyl ion. The cetyl pyridinimium bromide bathes these areas. The cetyl pyridine is believed by co-precipitate with the mucoprotein or mucopolysaccharides. The cetyl pyridine flocculants can also provide scrubbing action similar to a mild "abrasive", and the detergent wash then flushes these particles out as coalesced colloids.

The acid functions to flush out the detergent. At this point a further wash with hypochlorite weakens any remaining exposed bacteria and the 50% methanol treatment "soak" denatures the contaminating dehydrogenases as a dead-end complex. This sequence is most preferred embodiment of the invention, but other sequential series of steps can be employed within the scope of the invention.

EXAMPLE 2

Each of the series of cleansing agents in the wash cycle cartridge or package system is present to serve a specific function, so that the order of machine purges must necessarily follow exactly the order of the filled cuvettes. The entire contents of each compartment are completely aspirated. Each reagent aspiration is followed by a water or water/air wash in order to minimize one reagent reacting with another within the machine or in the waste collection vessel. Therefore, the contents of the waste collection vessel must frequently be emptied, or the waste line directly disposed into a sink with constantly running cold tap water. Generally, it is better to collect the waste in a collection vessel in order to inspect the debris and contaminants which come out of the machine, especially when the equipment is not maintained on a regular weekly basis.

The duration of each of the air/water wash intervals is of approximately the same duration as is each reagent aspiration. The procedure is as follows:

1. Insert all aspiration lines from the instrument into chamber #1 (reducer). These lines generally are water, substrate and sample. Allow the instrument to aspirate the entire contents of chamber #1.
2. With a polyethylene squeeze bottle or any other convenient appurtenance, fill the empty chamber #1 with distilled or de-ionized water. Allow the instrument to aspirate all of this water.
3. Aspirate now the empty air/water cell next for a few minutes. Discard now the contents of the collection vessel. Inspect for sediments and suspensoids as is considered desirable.
4. Aspirate now chamber #2, and repeat for chamber #2, Step 2. The collection vessel could be inspected now if so desired, but the contents of the waste vessel should be discarded after this step also. The reason for this is that both the reducer and oxidizer are rather reactive reagents and it would not be desirable for these two reagents to mix together.
5. From this point on—proceed to each successive chamber—preferably with intermittent water washes. However, these water washes are not critical. The important thing is that all of the reagents be completely aspirated from each successive chamber. The cartridge should then be discarded.
6. The machine should then aspirate water for at least five minutes.
7. The overall wash cycle should not take more than one hour. However, it should require a minimum of twenty (20) minutes.

A wash cycle procedure has been discovered for use with enzyme analyzers as a cleansing cycle of all internal plumbing, autodilutors, and the like, and further, a package system employed so that the weekly use of these disposable wash cycle cartridges will insure minimal contamination of microbes, inhibitors, receptors and residues. This package and process should greatly improve quality control in enzyme related analyses, especially in clinical laboratories.

A schematic drawing, FIG. 2, is also included as a part hereof to better illustrate the invention and the particular type of kit or assembly which is adapted for its successful use.

FIG. 2 (A, B, C, and D) are various views and illustrations of a typical wash cycle cartridge according to this invention. A large model of the cartridge is conveniently made of fused plastic by injection molding, for example. The solutions (reagents) are packaged and contained in the respective numbered compartments 1-6.

What is claimed is:

1. A programmed in situ wash cycle process procedure for cleaning microbial and enzyme contaminated equipment which comprises sequentially contacting said equipment with at least six chemical agents in the following numerical STEP order: (1) from about 2 to 10 wt. % of a chemical hypochlorite reducing agent, (2) from about 2 to 10 wt. % of a chemical peroxide oxidizing agent, (3) a from about 0.1 to 0.5 N concentration alkaline hydroxide solution, (4) a solution containing from 1 to 5% cetyl pyridinium bromide and from 0.05 to 0.2% cinnamic aldehyde, (5) a from about 10 to 50% polysulfonated alkyl detergent solution and (6) a from about 0.1 to 0.5 N concentration of a cleaning acid solution.

2. In a process for detecting heart attacks and septicemia in human patients by determination of creatine-phosphokinase-MB isoenzyme using analytical unstrumentation the imporovement which comprises subjecting the analytical instrumentation to a programmed wash cycle comprising sequentially contacting said instrumentation with at least six chemical agents in the following numerical step order: (1) a 2 to 10 wt. % solution of sodium hypochlorite, (2) a 2 to 10 wt. % solution of hydrogen peroxide, (3) an 0.1 to 0.5 N concentration solution of sodium hydroxide, (4) a solution containing from 1 to 5% cetyl pyridinium bromide, and from 0.05 to 0.2% cinnamic aldehyde, (5) a 10 to 50% solution of a polysulfonated detergent, and (6) an 0.1 to 0.5 N solution of hydrochloric acid.

3. The process of claim 1 in which the said reducing agent (1) is sodium hypochlorite, said oxidizing agent (2) is hydrogen peroxide, said alkaline solution (3) is a sodium hydroxide solution and said acid solution (6) is a solution of hydrochloric acid.

4. The process of claim 3 in which an air purge step is included between the steps for said reducing agent step and for said oxidizing agent step.

5. The process of claim 3 in which the process is used to clean contaminated laboratory equipment.

6. The process of claim 3 in which the process is used to clean contaminated industrial equipment.

7. The process of claim 3 in which the process is used to clean contaminated tubing and piping.

8. The method of claim 6 in which the individual solutions of each step in the programmed wash cycle are repeatedly recovered and recycled in their appropriate order in the programmed cycle.

9. A method for carrying out a cleaning and polishing system for cleaning and removing contaminating dehydrogenases and other ultra-violet interfering contaminants which comprises carrying out the method of claim 3 followed by soaking the equipment in about 50% methanol.

* * * * *